United States Patent
Pfleiderer et al.

(10) Patent No.: US 6,844,343 B1
(45) Date of Patent: Jan. 18, 2005

(54) N-SUBSTITUTED 4-AMINOPTERIDINES, SYNTHESIS AND USE THEREOF AS PHARMACEUTICAL AGENT

(75) Inventors: Wolfgang Pfleiderer, Constance (DE); Harald Schmidt, Giessen (DE); Lothar Fröhlich, Würzburg (DE); Peter Kotsonis, Würzburg (DE); Shahriyar Taghavi-Moghadam, Mainz (DE)

(73) Assignee: Vasopharm Biotech GmbH, Wurzburg (DE)

( * ) Notice: Subject to any disclaimer, the term of this patent is extended or adjusted under 35 U.S.C. 154(b) by 0 days.

(21) Appl. No.: 10/070,976

(22) PCT Filed: Sep. 11, 2000

(86) PCT No.: PCT/EP00/08833

§ 371 (c)(1),
(2), (4) Date: Jul. 19, 2002

(87) PCT Pub. No.: WO01/21619

PCT Pub. Date: Mar. 29, 2001

(30) Foreign Application Priority Data

Sep. 17, 1999 (DE) .......................................... 199 44 767

(51) Int. Cl.$^7$ ................... A61K 31/4985; C07D 475/08
(52) U.S. Cl. ........................................ 514/249; 544/260
(58) Field of Search ........................... 544/260; 514/249

(56) References Cited

U.S. PATENT DOCUMENTS

| | | | |
|---|---|---|---|
| 5,459,158 A | 10/1995 | Moore et al. ................ | 514/406 |
| 5,902,810 A | 5/1999 | Pfleiderer et al. ........... | 514/249 |

FOREIGN PATENT DOCUMENTS

| | | |
|---|---|---|
| DE | 41 20 247 A | 12/1992 |
| DE | 4120247 A 1 | 12/1992 |
| DE | 44 18 096 A | 11/1995 |
| DE | 44 18 097 A | 11/1995 |
| EP | 0 906 913 A | 4/1999 |
| EP | 0906913 | 4/1999 |
| WO | WO 94 14780 | 7/1994 |
| WO | WO 95/32203 | 11/1995 |
| WO | WO 00 39129 A | 7/2000 |

OTHER PUBLICATIONS

Froehlich et al., Chemical Abstracts, vol. 131:317316, 1999.*
S. Taghavi–Moghadam et al., "A New, General and Regioselective Method for the Synthesis of 2,6 Disubstituted 4–Aminopteridines", *Tetrahedran Letters*, 38(39), pp. 6835–6836 (1997).
U.S. patent application No. 60/113,989, filed Dec. 28, 1998, which is the priority document of WO 00 39129.
Ph.D. Thesis of S. Taghavi–Moghadam, Dec. 1996.
PCT Search Report of Jan. 23, 2001.
Derwent Abstract of EP 0 906 913A, 1999.
Derwent Abstract of DE 44 18 097 A, 1995.
Derwent Abstract of DE 41 20 247 A, 1992.

* cited by examiner

*Primary Examiner*—Richard L. Raymond
(74) *Attorney, Agent, or Firm*—Finnegan, Henderson, Farabow, Garrett, & Dunner LLP

(57) ABSTRACT

Compounds of formula (I), where preferably: A=a bridge of partial formula (II) or (III), $R^1$ and $R^2$=independently (substituted) alkyl, aryl or aralkyl, or together form a heterocycle, $R^3$=H, —CO-Alkyl, or —CO-Aryl, $R^4$=Aryl, —CO—O-Aryl or —CO-Aryl and $R^5$=H, are potent inhibitors of NO-synthase and are suitable as pharmaceutical agents of prophylaxis and treatment of disease states associates with a disturbed NO metabolism.

9 Claims, No Drawings

N-SUBSTITUTED 4-AMINOPTERIDINES, SYNTHESIS AND USE THEREOF AS PHARMACEUTICAL AGENT

This application is a national stage filing of International Application No. PCT/EP00/08833, filed Sep. 11, 2000. This application also claims the benefit of priority under 35 U.S.C. § 119(a) to German Patent Application No. 199 44 767.5, filed on Sep. 17, 1999.

The present invention relates to N-substituted 4-aminopteridines of the following general formula, a process for their preparation and their use for the prevention and treatment of diseases caused by a disturbed nitric oxide balance.

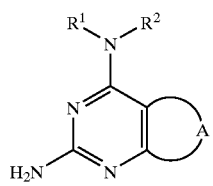

Nitric oxide (NO) is a ubiquitous bearer of physiological and pathophysiological functions (S. Moncada et al. *Pharmacol. Rev.* 43 (1991), 109–142). It has a relaxant effect on the smooth muscles of vessels and, in this way, is crucially involved in the regulation of blood pressure and the proliferation of vessel wall cells; it controls, via inhibition of platelet aggregation, the coagulation of blood and is involved as neuromodulator in the brain and spinal cord. NO likewise functions as messenger in the NANC nerves of the peripheral nervous system. The cytotoxic effect of NO is utilized by macrophages and a large number of other cells for defence against infections but also plays a part in the inflammatory reaction and autoimmune reaction.

Endogenous NO is produced with the aid of three different NO synthase isoenzymes from arginine (Kershaw, Ann. Rep. Med. Chem. 27 (1992) 69). All the isoenzymes require NADPH, flavin adenine dinucleotide, flavin mononucleotide and tetrahydrobiopterin as cofactors. They differ in their localization in the body, in their regulation by $Ca^{2+}$/calmodulin and in their inducibility by endotoxins and cytokines. The constitutive, calcium-dependent NO synthases are found, for example, in the endothelium (type III) and in the brain (type I) and are there involved in the regulation of blood pressure and coagulation and in conduction processes. The cytokine-inducible, calcium-independent isoform (type II) occurs in macrophages, smooth muscle cells and hepatocytes. It is able to produce relatively large amounts of NO over a long period and is thought to be responsible for inflammatory and autoimmune processes and the cytotoxic activity of macrophages.

A disturbed NO balance results in serious disorders and damages. Thus, excessive production of NO in septic or hemorrhagic shock leads to massive pathological falls in blood pressure. Excessive NO production is involved, for example, in the development of autoimmune diseases such as type 1 diabetes, and of atherosclerosis and is partly responsible for the glutamate-induced neurotoxicity following cerebral ischemia. High NO concentrations may in addition lead, through deamination of cytosine, to DNA damage and cancer. Selective inhibition of the NO synthases involved in the particular pathological states is therefore for the treatment or prevention of said diseases.

Only a few representatives of N-substituted 4-aminopterins have been disclosed in the chemical literature to date. All these representatives contain either a substituent differing from hydrogen in the 7-position of the pterin framework or an aminobenzoylglutamate residue analogous to folic acid in the 6-position of the pterin framework (see formulae (a) and (b) below for the pterin framework).

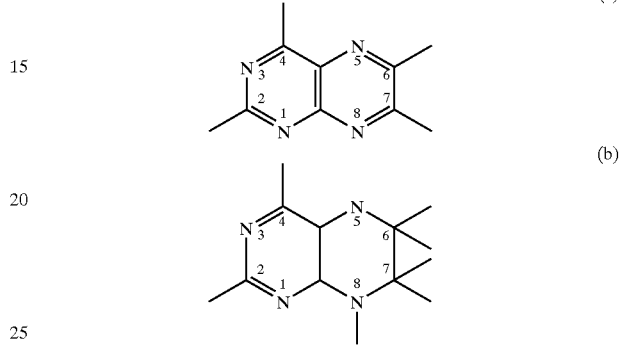

Extremely little information is available about the pharmacological effect of N-substituted 4-aminopterins: Dewey et al. (Biochem. Pharmacol. 23 (1974) 773) and Weinstock et al. (J. Med. Chem. 11 (1968) 573) report a potentially diuretic effect of 2,7-diamino-4-methylamino-6-phenylpteridine, Roth et al. (J. Am. Chem. Soc. 73 (1951) 1914) determined the antagonistic effect of various folic acid-analogous (2-amino-4-alkylaminopteridin-6-ylmethyl) aminobenzoylglutamates on *S. faecalis* R. The effect of these derivatives, which is characterized by the authors as "weak", is likely to be attributable to a large extent to the presence of the aminobenzoylglutamate, which is typical of such agents, in the 6-position of the pteridine.

There has likewise to date been only little discussion of the use of pterin analogues for inhibiting NO synthase (NOS) in the literature. The majority of published pharmacological approaches to NOS inhibition are based on a competitive effect on the substrate binding site of the enzyme for L-arginine via substrate analogues (see, for example, E. S. Furfine et al. J. Biol. Chem. 269 (1994) 26677).

Further potential NO synthase inhibitors which have been discussed in the literature are N-iminoethyl-ornithine (Mc Call et al., Br. J. Pharmacol. 102 (1991) 234), aminoguanidine (T. P. Misko et al., Eur. J. Pharmacol., 233 (1993) 119, EP547588-A1) and 7-nitro-indazole (P. K. Moore et al., Br. J. Pharmacol. 108 (1993) 296).

The effect of simple 6R-5,6,7,8-tetrahydrobiopterin analogues ($BH_4$ analogues) on NO production has been investigated by Stuehr et al. (J. Biol. Chem. 264 (1989) 20496), Giovanelli et al. (Proc. Natl. Acad. Sci. 88 (1991) 7091), M ülsch and Busse (J. Cardiovasc. Pharmacol. 17 (1991) S52), Sakai et al. (Mol. Pharmacol. 43 (1992) 6), Werner et al. (FEBS Letters 305 (1992) 160), Wachter et al. (Biochem. J. 289 (1993) 357) and by Hevel and Marletta (Biochemistry 31 (1992) 7160). According to these, $6S-BH_4$, $7-R/S-BH_4$, 6-methyl-5,6,7,8-tetrahydropterin and dihydrobiopterin are able to partly replace the natural cofactor. Biopterin, 6,7-dimethyl-5,6,7,8-tetrahydropterin, tetrahydrofolic acid, dihydrofolic acid, folic acid, tetrahydro-neopterin, dihydroneopterin, neopterin, methotrexate, pterin, 6-hydroxymethylpterin, xanthopterin and isoxanthopterin showed no significant effects. Only with 5-deaza-6-methyl-5,6,7,8-tetrahydropterin was it possible to achieve a weak inhibition of NO synthase. Overfeld et al. (Br. J. Pharmacol., 107 (1992) 1008) observed inhibition of NO production in intact rat alveolar macrophages by $BH_4$ and sepiapterin, which is presumably based on a feedback mechanism. Pterin-6-carboxylic acid showed no effect in these tests.

Bömmel et al. (J. Biol. Chem. 273 (1998) 33142 and Portland Press Proc. 15 (1998) 57) used pterins and photolabile pterin derivatives for characterizing the tetrahydrobiopterin binding site of NO synthase.

The use of pteridinones for inhibiting NO synthase is disclosed in WO-A-94/14780. EP-A-0,760,818 and EP-A-0,760,664 describe the use of a number of differently substituted pteridines and tetrahydro-pteridines for inhibiting NO synthase. The pterins and pteridines described therein are, however, still in need of improvement in relation to some properties such as activity, selectivity for particularly NO synthase isoforms and solubility.

Pfeiffer et al. (Biochem. J. 328 (1997) 349) describe 4-aminobiopterin as inhibitor of NO synthase (Biochem. J., 328 (1997) 349). These compounds have, inter alia, a free amino group in the 4-position and a side chain in the 6-position which is unaltered compared with the natural cofactor. Recently solved X-ray structures (B. R. Crane et al., Science 279 (1998) 2121) show interactions of these compounds with NO synthase.

It has now been found, surprisingly, that, in particular, pteridines whose amino group in the 4-position is substantially blocked by substituents, preferably by alkylation or dialkylation, and which is have in the 6-position a predominantly lipophilic group are potent inhibitors of NO synthase and, as such, can be used for the treatment of diseases associated with an increased NO level.

The pterins of the general formula I represent compared with the pterins disclosed in EP 0 760 818 and EP 0 760 664, a considerable and, in every respect, surprising advance especially in relation to the NO synthase-inhibiting effect, isoform selectivity and the sustained improvement in the solubility properties.

The present invention relates to compounds of the general formula I

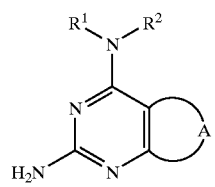

(I)

where
A is a bridge of the form

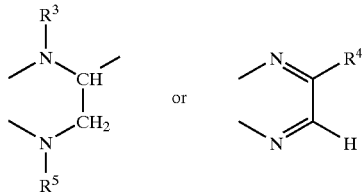

$R^1$ is hydrogen, alkyl, alkenyl, alkynyl, preferably $(C_1-C_{10})$-alkyl, cycloalkyl, cycloalkenyl, preferably $(C_3-C_8)$-cycloalkyl, cycloalkylalkyl, aryl, alkylaryl, preferably $(C_1-C_3)$-alkylaryl or arylalkyl, where the organic radicals, preferably the alkyl radicals, may be substituted by one or more substituents, preferably by substituents $R^6$, $R^2$ is, independently of $R^1$, alkyl, alkenyl, alkynyl, preferably $(C_1-C_{10})$-alkyl, cycloalkyl, cycloalkenyl, preferably $(C_3-C_8)$-cycloalkyl, cycloalkylalkyl, aryl, alkylaryl, preferably $(C_1-C_3)$-alkylaryl, or arylalkyl, where the organic radicals, preferably the alkyl radicals, may be substituted by one or more substituents, preferably by substituents $R^6$ $R^1$ and $R^2$ may, together with the nitrogen atom bearing them, form a 3–8-membered ring which may optionally contain 0, 1 or 2 further heteroatoms from the series N, O, S and which is optionally substituted by one or more radicals, preferably $R^6$ radicals, $R^3$ is hydrogen, —CO-alkyl, preferably —CO—$(C_1-C_7)$-alkyl, —CO-alkylaryl, preferably —CO—$(C_1-C_3)$-alkylaryl or —CO-aryl, $R^4$ is alkyl, alkenyl, alkynyl, preferably $(C_1-C_{10})$-alkyl, cycloalkyl, cycloalkenyl, preferably $(C_3-C_8)$-cycloalkyl, cycloalkylalkyl, aryl or alkylaryl, preferably $(C_1-C_3)$-alkylaryl, arylalkyl, —CO—O-alkyl, preferably —CO—O—$(C_1-C_5)$-alkyl, —CO—O-aryl, —CO-alkyl, preferably —CO—$(C_1-C_5)$-alkyl or —CO-aryl, where the organic radicals, preferably the alkyl radicals, may be substituted by one or more substituents, in particular by substituents $R^7$, $R^5$ is, independently of $R^3$, hydrogen, —CO-alkyl, preferably —CO— $(C_1-C_7)$-alkyl, —CO-alkylaryl, preferably —CO—$(C_1-C_3)$-alkylaryl or —CO-aryl, $R^6$ is —F, —OH, —O—$(C_1-C_{10})$-alkyl, —O-phenyl, —O—CO—$(C_1-C_{10})$-alkyl, —O—CO-aryl, —$NR^8R^9$, oxo, phenyl, —CO—$(C_1-C_5)$-alkyl, —$CF_3$, —CN, —$CONR^8R^9$, —COOH, —CO—O—$(C_1-C_5)$-alkyl, —CO—O-aryl, —$S(O)_n$—$(C_1-C_5)$ alkyl, —$SO_2$—$NR^8R^9$, $R^7$ has, independently of $R^6$, one of the meanings of $R^6$, $R^8$ is hydrogen or alkyl, preferably $(C_1-C_5)$-alkyl, $R^9$ is hydrogen, alkyl, preferably $(C_1-C_5)$-alkyl or aryl, preferably phenyl, aryl is preferably phenyl, naphthyl or heteroaryl, each of which may be unsubstituted or substituted, for example may be substituted by one or more identical or different substituents from the series halogen, alkyl, preferably $(C_1-C_5)$-alkyl or phenyl, —OH, —O-alkyl, preferably —O—$(C_1-C_5)$-alkyl, alkylenedioxy, preferably $(C_1-C_2)$-alkylenedioxy, —$N^8R^9$, —$NO_2$, —CO—$(C_1-C_5)$-alkyl, —$CF_3$, —CN, —$CONR^8R^9$, —COOH, —CO—O—$(C_1-C_5)$-alkyl, —$S(O)_n$—$(C_1-C_5)$-alkyl, —$SO_2$—$NR^8R^9$, heteroaryl is a 5- to 7-membered unsaturated heterocycle which contains one or more heteroatoms from the series O, N, S, n is 0, 1 or 2, in all their stereoisomeric and tautomeric forms and mixtures thereof in all ratios, and their physiologically acceptable salts, hydrates and esters.

If groups or substituents occur more than once in the compounds of the formula I, they may all, independently of one another, have the stated meanings and may in each case be identical or different.

Alkyl radicals may be straight-chain or branched. This also applies if they are present in other groups, for example in alkoxy groups, alkoxycarbonyl groups or; in amino groups, or if they are substituted. Alkyl radicals normally contain one to twenty carbon atoms, preferably one to ten carbon atoms.

Examples of alkyl groups are methyl, ethyl, propyl, butyl, pentyl, hexyl, heptyl, octyl, nonyl, decyl, the n-isomers of these radicals, isopropyl, isobutyl, isopentyl, sec-butyl, tert-butyl, neopentyl, 3,3-dimethylbutyl.

Examples of alkenyl radicals are straight-chain or branched hydrocarbon radicals which contain one or more double bonds. Alkenyl radicals normally contain two to twenty carbon atoms and one or two double bonds, preferably two to ten carbon atoms and one double bond.

Examples of alkynyl radicals are straight-chain or branched hydrocarbon radicals which contain one or more triple bonds. Alkynyl radicals normally contain two to twenty carbon atoms and one or two triple bonds, preferably two to ten carbon atoms and one triple bond.

Examples of alkenyl radicals are the vinyl radical, the 2-propenyl radical (allyl radical), the 2-butenyl radical and the 2-methyl-2-propenyl radical.

Examples of alkynyl radicals are the ethynyl radical, the 2-propynyl radical (propargyl radical) or the 3-butinyl radical.

Cycloalkyl radicals are saturated cyclic hydrocarbons which normally contain three to eight ring carbon atoms, preferably five or six ring carbon atoms. Cycloalkyl radicals may in turn be substituted.

Examples of cycloalkyl radicals are cyclopropyl, cyclobutyl, cyclopentyl, cyclohexyl, cycloheptyl and cycloctyl, all of which may also be substituted for example by one or more identical or different $(C_1–C_4)$-alkyl radicals, in particular by methyl. Examples of such substituted cycloalkyl radicals are 4-methylcyclo-hexyl or 2,3-dimethylcyclopentyl.

Cycloalkenyl radicals are unsaturated cyclic hydrocarbons which normally contain three to eight ring carbon atoms, preferably five or six ring carbon atoms. Cycloalkenyl radicals preferably have a double bond in the ring system. Cycloalkenyl radicals may in turn be substituted.

Cycloalkylalkyl radicals are saturated hydrocarbons which are derived from a cycloalkyl-substituted alkyl group. The cycloalkyl group normally has five to six ring carbon atoms. Examples of cycloalkylalkyl radicals are cyclopentylmethyl, cyclopentylethyl, cyclohexyl-ethyl and, in particular, cyclohexylmethyl. Cycloalkyl-alkyl radicals may in turn be substituted.

Aryl is a carbocyclic or heterocyclic aromatic radical, preferably phenyl, naphthyl or heteroaryl. Aryl radicals may be unsubstituted or substituted. Substituents are one or more identical or different monovalent organic radicals, for example or from the series halogen, alkyl, phenyl, —OH, —O-alkyl, alkylenedioxy, —NR$^8$R$^9$, —NO$_2$, —CO—$(C_1–C_5)$-alkyl, —CF$_3$, —CN, —CON$^8$R$^9$, —COOH, —CO—O—$(C_1–C_5)$-alkyl, —S(O)$_n$—$(C_1–C_5)$-alkyl, —SO$_2$—NR$^8$R$^9$.

Alkylaryl is an alkyl-substituted aryl radical, preferably $(C_1–C_3)$-alkylaryl, in particular methylphenyl.

Arylalkyl is an aryl-substituted alkyl radical, preferably phenylmethyl or 2-phenylethyl.

Heteroaryl or a heterocyclic aromatic radical is preferably a 5- to 7-membered unsaturated heterocycle which has one or more heteroatoms from the series O, N, S.

Examples of heteroaryls from which the radicals occurring in compounds of the formula I may be derived are pyrrole, furan, thiophene, imidazole, pyrazole, 1,2,3-triazole, 1,2,4-triazole, 1,3-oxazole, 1,2-oxazole, 1,3-thiazole, 1,2-thiazole, tetrazole, pyridine, pyridazine, pyrimidine, pyrazine, pyran, thiopyran, 1,4-dioxan, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine or 1,3-thiazepine.

The radicals derived from the heterocycles may be bonded via any suitable carbon atom. Nitrogen heterocycles which have a hydrogen atom (or a substituent) on a ring nitrogen atom, for example pyrrole, imidazole, etc, may also be bonded via a ring nitrogen atom, especially if the relevant nitrogen heterocycle is bonded to a carbon atom. A thienyl radical may, for example, be in the form of a 2-thienyl radical or 3-thienyl radical, a furan radical in the form of a 2-furyl radical or 3-furyl radical, a pyridyl radical in the form of a 2-pyridyl radical, 3-pyridyl radical or 4-pyridyl radical.

Halogen is fluorine, chlorine, bromine or iodine, preferably fluorine or chlorine.

$R^1$ is preferably hydrogen, $(C_2–C_4)$-alkyl which may be substituted by one or more substituents $R^6$, or $(C_1–C_2)$-alkylaryl, and $R^2$ is particularly preferably arylmethyl $R^2$ is preferably $(C_2–C_4)$-alkyl which may be substituted by one or more substituents $R^6$, or $(C_1–C_2)$-alkylaryl, and $R^2$ is particularly preferably arylmethyl in addition, $R^1$ and $R^2$ preferably form, together with the nitrogen atom bearing them, a 5–7-membered ring which preferably contains no or only one other heteroatom from the series N, O, S. Very particularly preferred rings of this type are pyrrolidine, piperidine, morpholine, dimethyl-morpholine, thiomorpholine or N—$(C_1–C_2)$-alkylpiperazine, where these rings themselves may also be substituted, for example by —OH, —O—$(C_1–C_3)$-alkyl, —NR$^8$R$^9$ or —COOH.

$R^3$ is preferably hydrogen, CO—$(C_1–C_3)$-alkyl or CO-aryl, and $R^3$ is very particularly preferably hydrogen.

$R^4$ is preferably aryl, $(C_1–C_3)$-alkyl which may be substituted by one or more substituents $R^7$, or —CO—O-aryl. Particularly preferred $R^4$ radicals are aryl and 1,2-dihydroxypropyl.

$R^5$ is preferably hydrogen.

$R^6$ is preferably —OH, —O—$(C_1–C_3)$-alkyl, —NR$^8$R$^9$ or —COOH.

$R^7$ is preferably —OH, —O—$(C_1–C_{10})$-alkyl, phenoxy, oxo, particularly preferably —OH, decyloxy and phenoxy, aryl is preferably phenyl, thienyl, furyl and pyridyl, and phenyl is particularly preferred, all of which can be substituted as described. Preferred substituents are $(C_1–C_3)$-alkyl, halogen and $(C_1–C_3)$-alkyloxy and ($C_1$–$C_2$)-alkylenedioxy. The preferred number of substituents on aryl radicals is 0, 1 or 2; phenyl substituents are preferably in the meta or para position, and in the case of two substituents in the 3 and 4 positions.

n is preferably 0 and 2

Concerning so-called structure-activity relations, it must be stated that in this connection in particular the 4- and the 6-positions of the pterin framework appear to be of relevance. In the case of tetrahydropterins (compare formula (b)), for example large-volume substituents in the 6-position such as, for example, substituted phenyl, increase the activity of the agents. In the case of aromatic structures (compare formula (a)), an increase in activity is observed preferentially when the amino substituent in the 4-position is dialkylated or diaralkylated and the 6-position is arylated.

The invention encompasses all possible enantiomers and diastereomers of the compounds of the general formula I, as well as mixtures of two or more stereoisomeric forms, for example mixtures of enantiomers and/or diastereomers, in all ratios.

The invention thus encompasses enantiomers in enantiopure form, both as levorotatory and as dextrorotatory antipodes, in the form of racemates and in the form of mixtures of the two enantiomers in all ratios. If a cis/trans isomerism is present, both the cis-form and the trans-form and mixtures of these forms in all ratios are encompassed by the invention. Individual stereoisomers can, if desired, be prepared by fractionating a mixture by conventional methods, for example by chromatography or crystallization, by use of stereochemically pure starting materials in the synthesis or by stereoselective synthesis. A separation of stereoisomers may optionally be preceded by a derivatization. The separation of the mixture of stereoisomers can take place at the stage of compounds of the formula I or at the stage of an intermediate during the synthesis. If mobile hydrogen atoms are present, the present invention also encompasses all tautomeric forms of the compounds of the formula I.

The invention also encompasses the corresponding physiologically or toxicologically acceptable salts, in particular the pharmaceutically usable salts. Thus, the compounds of the formula I which contain acidic groups may, for example, be in the form of alkali metal salts, alkaline earth metal salts or of ammonium salts and these groups can be used according to the invention. Examples of such salts are sodium salts, potassium salts, calcium salts, magnesium salts or salts with ammonia or organic amines such as, for example, ethylamine, ethanolamine, triethanolamine or amino acids.

Compounds of the formula I which contain one or more basic, that is protonatable, groups may be in the form of their acid addition salts with physiologically acceptable inorganic or organic acids and used according to the invention, for example as salts with hydrochloric acid, hydrobromic acid, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid etc.

If the compounds of the formula I contain both acidic and basic groups in the molecule, the invention also includes inner salts or betaines (zwitterions) in addition to the salt forms described.

Salts can be obtained from compounds of the formula I by conventional processes known to the skilled worker, for example by combining with an organic or inorganic acid or base in a solvent or dispersant, or else by anion exchange or cation exchange from other salts. The present invention further encompasses all solvates of compounds of the formula I, for example hydrates or adducts with alcohols, and derivatives of the compounds of the formula I such as, for example, esters, and prodrugs and active metabolites.

Compounds according to the invention of the general formula I can be obtained as shown in the following synthesis scheme

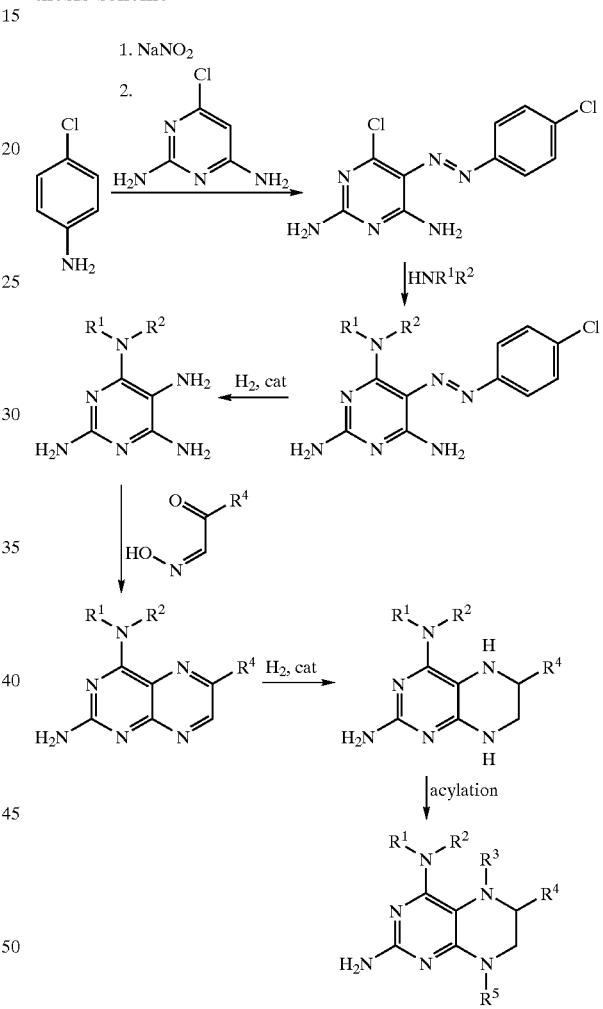

The scheme is explained in detail below:

To synthesize compounds of the general formula I, 2,6-diamino-4-chloro-5-p-chlorophenylazopyrimidine (II) as pure substance or in a solvent such as, for example, DMF, toluene or tetrahydrofuran is reacted with a 2–20-fold excess of an amine of the general formula $HNR^1R^2$ (III) at a temperature which is preferably between room temperature (RT) and the boiling point of the solvent. Alternatively, the reaction can also be carried out with an equimolar amount of the amine in the presence of an auxiliary base such as, for example, triethylamine or Hünig base.

The resulting 2,6-diamino-4-(subst. amino)-5-p-chlorophenylazopyrimidines (IV) are hydrogenated in a solvent such as, for example, methanol, ethanol or water, preferably in the presence of an acid such as, for example, HCl or acetic acid, or in the presence of a base such as, for example, ammonia, with the aid of a catalyst such as, for example, Raney nickel, platinum dioxide or palladium on carbon under a pressure of between 1 and 200 atm of hydrogen.

The 2,5,6-triamino-(subst. amino)pyrimidines (V) obtained in this way are then mixed in a solvent such as, for example, methanol, ethanol, DMF or water with the particular glyoxal monoxime (VI) containing the radical $R^4$, and this mixture is stirred until conversion is complete at a temperature which is between RT and the boiling point of the solvent employed. After cooling, the suspension or solution is made basic with a base such as, for example, ammonia, and the precipitate which has separated out is filtered off with suction, washed with water and dried.

A solution of the resulting pteridine is hydrogenated in a solvent such as THF, methanol or ethanol with the assistance of a catalyst such as, for example, Raney nickel, platinum dioxide or palladium on carbon under a pressure of between 1 and 200 atm of hydrogen. Further derivatization to introduce the substituents $R^3$ and/or $R^4$ can be carried out by standard processes for acylations which are known to the skilled worker.

The abovementioned reactions for preparing 4-aminopteridine derivatives are described in principle, for example, in WO-A-97/21711.

The present invention likewise relates to the abovementioned process for preparing compounds of the formula I.

The present invention likewise relates to compounds of the formula V

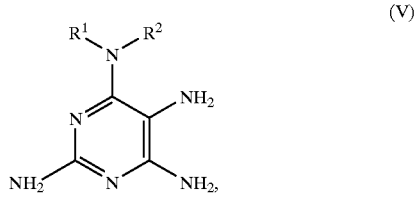

In this, $R^1$ and $R^2$ have the meaning defined hereinbefore.

Diseases which are produced by an increased NO level and which thus can be treated according to the invention with compounds of the general formula I or which can be prevented using the latter are, in particular, pathological falls in blood pressure like those occurring in septic or hemorrhagic shock, in tumor therapy with cytokines or in cirrhosis of the liver, or autoimmune diseases such as type I diabetes, and atherosclerosis. In addition inflammatory diseases such as rheumatoid arthritis and, in particular, ulcerative colitis, and insulin-dependent diabetes mellitus and transplant rejection reactions.

The following disorders are also associated with an increased production of nitric oxide and can be treated according to the invention. In the cardiovascular system these are atherosclerosis, post-ischaemic reperfusion damage, myocarditis based on coxsackie virus infection and cardiomypathy; in the central nervous system types of neuritis, encephalomyelitis, viral neurodegenerative disorders, Alzheimer's disease, hyperalgesia, epilepsy and migraine; in the renal system acute renal failure and glomerulonephritis.

In addition, areas of application of compounds of the general formula I are also treatments in the region of the stomach and of the uterus/placenta and influencing the motility of sperm.

Compounds of the formula I and their physiologically acceptable salts, hydrates, esters and adducts can thus be used in animals, preferably in mammals, and in particular in humans, as pharmaceuticals on their own, or in mixtures with one another or together with other agents. The present invention therefore also relates in particular to the use of compounds of the formula I and their physiologically acceptable salts, hydrates and esters for producing a medicament for the therapy or prophylaxis of the aforementioned pathological states, and to the use for producing a medicament for lowering or normalizing an NO level.

The invention likewise relates to the use of the compounds of the formula I and their physiologically acceptable salts, hydrates and esters for inhibiting NO synthase, to their use for the therapy or prophylaxis of the aforementioned pathological states and to their use for normalizing a disturbed NO balance.

Likewise encompassed are pharmaceuticals which comprise the compounds of the formula I, their physiologically acceptable salts, esters and hydrates and esters on their own, in mixtures with one another or together with other agents in addition to conventional excipients and additives.

Examples of such other therapeutically active substances are: β-receptor blockers such as, for example, propanolol, pindolol, metoprolol; vasodilators such as, for example, carbocromen; sedatives such as, for example, barbituric acid derivatives, 1,4-benzo-diazepines and meprobamate; diuretics such as, for example, chlorothiazide; cardiotonic agents such as, for example, digitalis products; agents which lower blood pressure, such as, for example, hydralazine, dihydralazine, ACE inhibitors, prazosin, clonidine, rauwolfia alkaloids; agents which lower the fatty acid level in the blood, such as, for example, bezafibrate, fenofibrate; agents for thrombosis prophylaxis such as, for example, phenprocoumon; anti-inflammatory substances such as, for example, corticosteroids, salicylates, or propionic acid derivatives such as, for example, ibuprofen; antibiotics such as, for example, penicillins or cephalosporins; NO donors such as, for example, organic nitrates or sydnone imines.

Pharmaceuticals of the present invention can be administered orally, for example in the form of pills, tablets, film-coated tablets, sugar-coated tablets, granules, hard and soft gelatin capsules, aqueous, alcoholic or oily solutions, syrups, emulsions or suspensions, or rectally, for example in the form of suppositories. The administration can, however, take place parenterally, for example subcutaneously, intramuscularly or intravenously in the form of injection solutions or infusion solutions. Further suitable administration forms are, for example, percutaneous or topical administration, for example in the form of ointments, tinctures, sprays or transdermal therapeutic systems, or inhalational administration in the form of nasal sprays or aerosol mixtures, or, for example, microcapsules, implants or rods. The preferred mode of administration depends, for example, on the disease to be treated and its severity.

The medicaments according to the invention can be produced by the standard processes known for producing pharmaceutical products.

For this purpose, one or more compounds of the formula I and/or their physiologically acceptable salts, esters and hydrates are brought together with one or more solid or liquid pharmaceutical carriers and/or additives or excipients and, if desired, in combination with other active pharmaceutical ingredients with therapeutic or prophylactic action into a suitable administration form or dosage form, which can then be used as pharmaceutical in human medicine or veterinary medicine. The pharmaceutical products comprise a therapeutically or prophylactically effective dose of the compounds of the formula I and/or their physiologically acceptable salts, esters and hydrates, which normally amounts to from 0.5 to 90% by weight of is the pharmaceutical product.

To produce, for example, pills, tablets, sugar-coated tablets and hard gelatin capsules it is possible to use lactose, starch, for example corn starch or starch derivatives, talc, stearic acid or salts thereof etc. Carriers for soft gelatin capsules and suppositories are for example fats, waxes, semisolid and liquid polyols, natural or hydrogenated oils etc. Examples of carriers suitable for producing solutions, for example injection solutions, or emulsions or syrups are water, physiological saline, alcohols such as ethanol, glycerol, polyols, sucrose, invert sugar, glucose, mannitol, vegetable oils etc. The compounds of the formula I and their physiologically acceptable salts, esters and hydrates may also be lyophilized, and the resulting lyophilizates can be used, for example, for producing products for injection or products for infusion. Examples of carriers suitable for microcapsules, implants or rods are mixed polymers of glycolic acid and lactic acid.

The pharmaceutical products may besides the active ingredients and carriers also comprise conventional additives, for example fillers, disintegrants, binders, lubricants, wetting agents, stabilizers, emulsifiers, dispersants, preservatives, sweeteners, colorants, flavoring or aromatizing agents, thickeners, diluents, buffer substances, also solvents or solubilizers or means to achieve a depot effect, salts to alter the osmotic pressure, coating agents or antioxidants.

The dosage of the active ingredient of the formula I to be administered, and/or of a physiologically acceptable salt, ester or hydrate thereof depends on the individual case and should be adapted to the individual circumstances for an optimal effect in the conventional way. Thus, it depends on the nature and severity of the disease to be treated and on the sex, age, weight and individual response of the human or animal to be treated, on the potency and duration of action of the compounds employed, on whether the therapy is acute or chronic or the aim is prophylaxis, or on whether other active ingredients are administered in addition to compounds of the formula I. In general, a daily dose of about 0.01 to 100 mg/kg, preferably 0.1 to 10 mg/kg, in particular 0.3 to 5 mg/kg (in each case mg per kg of body weight) is appropriate on administration to an adult weighing about 75 kg to achieve the desired effect. The daily dose may be administered in a single dose or, especially on administration of larger amounts, be divided into a plurality of, for example two, three or four, single doses. It may, depending on the individual characteristics, be necessary where appropriate to deviate upward or downward from the stated daily dose. Pharmaceutical products normally contain 0.2 to 500 mg, preferably 1 to 200 mg, of active ingredient of the formula I and/or its physiologically acceptable salts.

The compounds of the formula I inhibit the various isoforms of NO synthase mainly through binding in the tetrahydrobiopterin binding cavity of the enzyme. Because of this property, they may be employed not only as active pharmaceutical ingredients in human medicine and veterinary medicine but also as scientific tool or as aid for biochemical investigations in which such an inhibition of NO synthase is intended, and for diagnostic purposes, for example in the in vitro diagnosis of cell samples or tissue samples. The compounds of the formula I and their salts, esters or hydrates may also be used as intermediates for preparing other active pharmaceutical ingredients.

EXAMPLES

The following preparation methods and examples illustrate the invention without restricting it:

2,6-Diamino-4-chloro-5-p-chlorophenylazopyrimidine

A solution of p-chloroaniline (25.5 g, 0.2 moles) in 6 N HCl (100 mL) was cooled to 0–5° C. and then a solution of $NaNO_2$ (13.8 g, 0.2 moles) in water (40 ml) was added dropwise with stirring. After completion of the addition, the solution was stirred for a further min, and the progress of the reaction was checked with the aid of iodine/starch paper (blue coloration). The excess $HNO_2$ was destroyed by adding urea (5 g). The diazonium salt solution was poured into a solution of 2,6-diamino-4-chloropyrimidine (26.0 g, 0.18 moles) in water (500 mL) and stirred for 30 min. Potassium acetate (70 g) was then added, and the mixture was stirred at room temperature for 16 hours. The precipitated product was filtered off with suction, washed with $H_2O$ and dried over $P_4O_{10}$ in a desiccator in vacuo. Yield: 44.0 g (81%) of yellow solid. Recrystallization from $DMF/H_2O$, m.p.: 268° C.

2,6-Diamino-4-alkylamino-5-p-chlorophenylazopyrimidines

General Procedure:

A solution of 2,6-diamino-4-chloro-5-p-chlorophenylazopyrimidine (5.0 g, 16.6 mmol) and 10 g of the amine in DMF (50 mL) was stirred in an oil bath at 70° C. for 5 hours. Addition of water (50 mL) was followed by cooling and filtering off the precipitate with suction, washing with water, drying and recrystallizing from EtOH or acetone/water.

The following were obtained in this way:

1.) 2,6-diamino-4-diethylamino-5-p-chlorophenylazopyrimidine, m.p.: 145–148° C.
2.) 2,6-diamino-4-dibenzylamino-5-p-chlorophenylazopyrimidine, m.p.: 185–186° C.
3.) 2,6-diamino-4-(morpholin-4-yl)-5-p-chlorophenylazopyrimidine, m.p.: 219–221° C.
4.) 2,6-diamino-4-(piperidin-1-yl)-5-p-chlorophenylazopyrimidine, m.p.: 199–201° C.
5.) 2,6-diamino-4-(4-methylpiperazin-1-yl)-5-p-chlorophenylazopyrimidine, m.p.: 218–220° C.

2,5,6-Triamino-4-alkylaminopyrimidines (hydrochlorides)

General Procedure:

A solution of 10 mmol of the 2,6-diamino-4-alkylamino-5-p-chlorophenylazopyrimidine in methanol (70 mL) and conc. ammonia (10 mL) was reduced in a shaking apparatus in the presence of the catalyst Raney nickel (3.5 g) under an $H_2$ atmosphere for 2 days. The catalyst was filtered off under an argon atmosphere and the filtrate was evaporated to dryness in vacuo. The residue was treated with ether to remove the p-chloro-aniline, and the remaining solid was stirred with methanolic HCl (10%, 50 mL) overnight. The dihydrochloride salt was filtered off with suction and dried over KOH in a desiccator in vacuo.

The following were obtained in this way:

6.) 2,5,6-triamino-4-diethylaminopyrimidine dihydrochloride, m.p.: 138–142° C.

7.) 2,5,6-triamino-4-dibenzylaminopyrimidine dihydrochloride, m.p.: 165–167° C.

8.) 2,5,6-triamino-4-(morpholin-4-yl)-pyrimidine dihydrochloride, m.p.: 215–218° C. (decomposition)

9.) 2,5,6-triamino-4-(piperidin-1-yl)-pyrimidine dihydrochloride, m.p.: 238–242° C.

10.) 2,5,6-triamino-4-(4-methylpiperazin-1-yl)-pyrimidine trihydrochloride, m.p.: 226–230° C. (decomposition)

2-Amino-4-alkylamino-6-($R^4$)-pteridines
General Procedure:

A solution of the arylglyoxal monoxime (7.5 mmol) containing the radical $R^4$ in MeOH (10 mL) was added dropwise to a boiling solution of 2,5,6-triamino-4-alkylaminopyrimidine dihydrochloride salt (5 mmol) in MeOH (20 mL), and this mixture was boiled under reflux for 3 hours. After cooling, the suspension or solution was adjusted to pH 9–10 with conc. ammonia, and the precipitate which separated out was filtered off with suction, washed with water and dried. The crude product was recrystallized from EtOH and DMF/$H_2O$.

The following were obtained in this way:

11.) 2-amino-4-(dimethylamino)-6-phenylpteridine, m.p.: 247–250° C.

12.) 2-amino-4-(dimethylamino)-6-(4-methylphenyl)-pteridine, m.p.: 251–256° C.

13.) 2-amino-4-(dimethylamino)-6-(4-methoxyphenyl)-pteridine, m.p.: 280–284° C. (decomposition)

14.) 2-amino-4-(dimethylamino)-6-methoxymethyl-pteridine, m.p.: 237–239° C.

15.) 2-amino-4-(diethylamino)-6-phenylpteridine hydrate, m.p.: 203–205° C.

16.) 2-amino-4-(diethylamino)-6-(4-chlorophenyl)-pteridine dihydrate, m.p.: 250–254° C. (decomposition)

17.) 2-amino-4-(diethylamino)-6-(4-methoxyphenyl)-pteridine hydrate, m.p.: 220–222° C.

18.) 2-amino-4-(diethylamino)-6-(3,4-dimethoxyphenyl)-pteridine hydrate, m.p.: 182–185° C.

19.) 2-amino-4-(dibenzylamino)-6-phenylpteridine dihydrate, m.p.: 225–227° C.

20.) 2-amino-4-(dibenzylamino)-6-(4-chlorophenyl)-pteridine dihydrate, m.p.: 250–253° C.

21.) 2-amino-4-(dibenzylamino)-6-(4-methoxyphenyl)-pteridine, m.p.: 245–247° C.

22.) 2-amino-4-(dibenzylamino)-6-(3,4-dimethoxyphenyl)-pteridine hemihydrate, m.p.: 200–201° C.

23.) 2-amino-4-(di-n-propylamino)-6-phenylpteridine trihydrate, m.p.: 177–178° C.

24.) 2-amino-4-(di-n-propylamino)-6-(4-chlorophenyl)-pteridine trihydrate, m.p.: 189–192° C. (decomposition)

25.) 2-amino-4-(di-n-propylamino)-6-(4-methoxyphenyl)-pteridine hydrate, m.p.: 207–210° C. (decomposition)

26.) 2-amino-4-(di-n-propylamino)-6-(3,4-dimethoxyphenyl)pteridine hydrate, m.p.: 158–160° C.

27.) 2-amino-4-(morpholin-4-yl)-6-phenylpteridine hydrate, m.p.: 224–227° C. (decomposition)

28.) 2-amino-4-(morpholin-4-yl)-6-(4-chlorophenyl)-pteridine hydrochloride hydrate, m.p.: 252–254° C. (decomposition)

29.) 2-amino-4-(morpholin-4-yl)-6-(4-methoxyphenyl)-pteridine hydrochloride hydrate, m.p.: 238–240° C. (decomposition)

30.) 2-amino-4-(morpholin-4-yl)-6-(3,4-dimethoxy-phenyl) pteridine trihydrate, m.p.: 218–220° C. (decomposition)

31.) 2-amino-4-(piperidin-1-yl)-6-phenylpteridine dihydrate, m.p.: 209–211° C.

32.) 2-amino-4-(piperidin-1-yl)-6-(4-chlorophenyl)-pteridine dihydrate, m.p.: 245–247° C. (decomposition)

33.) 2-amino-4-(piperidin-1-yl)-6-(4-methoxyphenyl)-pteridine hydrate, m.p.: 211–214° C. (decomposition)

34.) 2-amino-4-(piperidin-1-yl)-6-(3,4-dimethoxy-phenyl) pteridine hydrochloride dihydrate, m.p.: 238–241° C. (decomposition)

35.) 2-amino-4-(4-methylpiperazin-1-yl)-6-phenyl-pteridine hemihydrate, m.p.: 245–247° C. (decomposition)

36.) 2-amino-4-(4-methylpiperazin-1-yl)-6-(4-chloro-phenyl)pteridine hemihydrate, m.p.: 277–279° C. (decomposition)

37.) 2-amino-4-(4-methylpiperazin-1-yl)-6-(4-methoxy-phenyl)pteridine hemihydrate, m.p.: 228–230° C. (decomposition)

38.) 2-amino-4-(4-methylpiperazin-1-yl)-6-(3,4-di-methoxyphenyl)pteridine dihydrate, m.p.: 148–151° C. (decomposition)

39.) 2-amino-4-(pyrrolidin-1-yl)-6-(4-methoxyphenyl)-pteridine dihydrate, m.p.: 243–246° C. (decomposition)

2-Amino-4-alkylamino-6-($R^4$)-5,6,7,8-tetrahydro-pteridines
General Procedure:

A solution of pteridine (3 mmol) to be reduced in THF (25 ml) was agitated catalytically with $PtO_2$ (0.10 g)/$H_2$ in a shaking apparatus until hydrogen uptake ceased. The catalyst was filtered off, the filtrate was evaporated to dryness, and the residue was treated with methanolic HCl with stirring for several hours. The crystals which formed were filtered off with suction, washed with ether and dried in a desiccator in vacuo.

The following were obtained in this way:

40.) 2-amino-4-(morpholin-4-yl)-6-(4-methoxyphenyl)-5,6,7,8-tetrahydropteridine hydrochloride hemi-hydrate, m.p.: 219–222° C.

41.) 2-amino-4-(morpholin-4-yl)-6-(3,4-dimethoxy-phenyl)-5,6,7,8-tetrahydropteridine hydrochloride hydrate, m.p.: 168° C.

42.) 2-amino-4-(morpholin-4-yl)-6-phenyl-5,6,7,8-tetrahydropteridine dihydrochloride hemihydrate, m.p.: 200–203° C.

43.) 2-amino-4-(piperidin-1-yl)-6-(4-chlorophenyl)-5,6,7,8-tetrahydropteridine trihydrochloride hydrate, m.p.: 170° C.

44.) 2-amino-4-(piperidin-1-yl)-6-(4-methoxyphenyl)-5,6,7,8-tetrahydropteridine trihydrochloride hydrate, m.p.: 218–220° C.

45.) 2-amino-4-(piperidin-1-yl)-6-phenyl-5,6,7,8-tetrahydropteridine dihydrochloride dihydrate, m.p.: 178–182° C.

46.) 2-amino-4-(di-n-propylamino)-6-phenyl-5,6,7,8-tetrahydropteridine trihydrochloride hydrate, m.p.: 115° C.

47.) 2-amino-4-(di-n-propylamino)-6-(4-methoxyphenyl)-5,6,7,8-tetrahydropteridine dihydrochloride dihydrate, m.p.: 120° C.

48.) 2-amino-4-(diethylamino)-6-(4-chlorophenyl)-5,6,7,8-tetrahydropteridine dihydrochloride hemi-hydrate, m.p.: 138° C.

49.) 2-amino-4-(cyclohexylmethylamino)-6-(4-chlorophenyl)-5,6,7,8-tetrahydropteridine dihydro-chloride hydrate, m.p.: 160° C.

The inhibition of the activity of purified nitric oxide synthase (NOS) by compounds of the general formula I can be determined as follows.

In this activity assay the L-citrulline which is a coproduct of the formation of NO by purified NOS is quantitatively measured. $^3$H-radiolabeled L-arginine is employed as substrate of the enzyme reaction and is converted into $^3$H-L-citrulline and NO. After completion of the enzyme incubation, generated L-citrulline is removed from unused L-arginine by ion exchange chromatography from the reaction mixture; the $^3$H activity measured by liquid scintillation then is corresponds to the amount of L-citrulline, which is a direct measure of the activity of NOS.

The basic medium for carrying out the enzyme reaction is TE buffer (triethanolamine, EDTA, pH 7.0).

The final volume of each incubation is 100 µl. The reaction mixture is obtained by mixing the following 6 components on ice:

1. "REA-Mix" (pH 7.0) which contains triethanolamine, calcium chloride, magnesium chloride, EDTA, L-arginine, calmodulin and flavin adenine dinucleotide (FAD);
2. freshly prepared stock solution of β-nicotinamide adenine dinucleotide phosphate, reduced form (NADPH);
3. (6R)-5,6,7,8-tetrahydro-L-biopterin dihydro-chloride stock solution (BH$_4$) or —for experiments without BH$_4$- instead TE buffer;
4. purified NO synthase from pig cerebellum or from pig liver;
5. L-[2,3,4,5-$^3$H]-arginine hydrochloride stock solution (1.526 TBq/mmol);
6. substance to be tested.

The final concentrations of the components in the incubation volume of 100 µl are:

Triethanolamine 50 mM, EDTA 0.5 mM, CaCl$_2$ 226 µM, MgCl$_2$ 477 µM, L-arginine 50 µM, calmodulin 0.5 µM, FAD 5 µM, NADPH 1 mM, BH$_4$ (if added) 2 µM, substance to be tested 100 µM.

After mixing of the components on ice, the reaction mixture was immediately incubated in a water bath at 37° C. for 15 minutes. For determination of the IC$_{50}$ values it was incubated in the presence of 5 kU/ml catalase for 45 minutes. After this incubation time, the reaction was stopped by addition of 900 µl of ice-cold "stop buffer" (20 mM sodium acetate, 2 mM EDTA, pH 5.5), and the mixture (total volume now 1.0 ml) was placed on ice. To remove the unreacted $^3$H-L-arginine, the mixture was loaded onto an ion exchange column with 0.8 ml of Dowex AG 50 WX-8 (100–200 mesh) which has previously been washed and equilibrated with 2 ml of stop buffer. After loading of the sample, the column was eluted twice with 1 ml of water each time. The flow-through of the sample and the eluate were collected in scintillation vessels and purified (total volume 3 ml). 9 ml of scintillator solution were added to the 3 ml of aqueous measurement solution, and the homogeneous mixture was measured in a Tricarb 2500 TR (Packard) liquid scintillation counter for 1 minute for each sample. The activity found with the substance to be tested has been stated as a percentage of the activity of the control. Each substance was tested for an antagonistic effect in a concentration of 100 µM in the presence of 2 µM tetrahydrobiopterin, and for an agonistic effect on NOS in the absence of tetrahydrobiopterin.

All incubations were carried out on triplicates. Each experiment was repeated three times with different enzyme preparations. Some results are indicated in the following Table 1.

TABLE 1

| Example | Remaining activity (% of V$_{max}$) | IC$_{50}$ (µM) |
|---|---|---|
| 11 | 92 ± 11 | — |
| 12 | 15 ± 7 | 75 |
| 13 | 13 ± 4 | 74 |
| 15 | 75 ± 3 | — |
| 16 | 42 ± 10 | — |
| 17 | 2 ± 0.1 | 45 |
| 18 | 23 ± 4 | — |
| 19 | 0 ± 0.05 | 3 |
| 20 | 0 | 3.5 |
| 21 | 0 ± 0.05 | 5 |
| 22 | 0 | 2 |
| 23 | 77 ± 16 | — |
| 24 | 7 ± 4 | — |
| 25 | 25 ± 12 | — |
| 26 | 0 | 39 |
| 27 | 41 ± 8 | 82 |
| 28 | 3 ± 1.5 | — |
| 29 | 5 ± 0.1 | 34 |
| 30 | 5 ± 3 | — |
| 31 | 0 ± 0.05 | 62 |
| 32 | 3 ± 1 | — |
| 33 | 7 ± 0.2 | 50 |
| 34 | 0 | 44 |
| 35 | 83 ± 1 | — |
| 36 | 64 ± 9 | — |
| 37 | 84 ± 5 | — |
| 38 | 99 ± 16 | — |
| 39 | 30 ± 5 | — |
| 40 | 66 ± 14 | — |
| 41 | 68 ± 11 | — |
| 42 | 51 ± 3 | — |
| 43 | 0 | 13 |
| 44 | 0 | 42 |
| 45 | 0 | 6 |
| 46 | 8 ± 0.05 | — |
| 47 | 0 | 34 |
| 48 | 0 | 8 |
| 49 | 0 | 5 |

In addition, the relative selectivities of the antipterin inhibitors for the three known human NOS isoforms were measured. So doing, the IC$_{50}$ values for NOS-II/NOS-I and NOS-III/NOS-I were formed (compare Table 2).

The data show that the substances have an increased selectivity for inhibition of NOS-I relative to NOS-II and an increased selectivity relative to NOS-III.

TABLE 2

| Substance Example | NOS isoform | Activity (% of control) | IC$_{50}$ (µM) | Ratio NOS-II/I | Ratio NOS-III/I |
|---|---|---|---|---|---|
| 21 | NOS-I | 27 ± 1 | 18.7 | 21.3 | 5.3 |
|  | NOS-II | 81 ± 6 | 400$^a$ |  |  |
|  | NOS-III | 68 ± 2 | 100 |  |  |
| 45 | NOS-I | 0 ± 0 | 22.0 | 3.7 | 0.6 |
|  | NOS-II | 50 ± 2 | 81.5 |  |  |
|  | NOS-III | 11 ± 1 | 14.2 |  |  |
| 46 | NOS-I | 1 ± 0.1 | 18.7 | 10.7 | 2.9 |
|  | NOS-II | 68 ± 1 | 200$^a$ |  |  |
|  | NOS-III | 27 ± 0.2 | 53.4 |  |  |

TABLE 2-continued

| Substance Example | NOS isoform | Activity (% of control) | IC$_{50}$ ($\mu$M) | Ratio NOS-II/I | Ratio NOS-III/I |
|---|---|---|---|---|---|
| 47 | NOS-I | 0 ± 0.1 | 7.4 | 33.8 | 8.6 |
|  | NOS-II | 78 ± 0.4 | 250$^a$ |  |  |
|  | NOS-III | 31 ± 3 | 63.6 |  |  |
| 48 | NOS-I | 2 ± 0 | 41.5 | 7.2 | 1.1 |
|  | NOS-II | 74 ± 4 | 300$^a$ |  |  |
|  | NOS-III | 27 ± 1 | 45.4 |  |  |
| 49 | NOS-I | 0 ± 0.1 | 4.9 | 40.8 | 7.3 |
|  | NOS-II | 78 ± 6 | 200$^a$ |  |  |
|  | NOS-III | 18 ± 1 | 36 |  |  |

$^a$Enzyme inhibition not complete up to 300 $\mu$M (IC$_{50}$ values extrapolated).

What is claimed is:
1. A compound of the formula (Ia), (Ib) or (Ic),

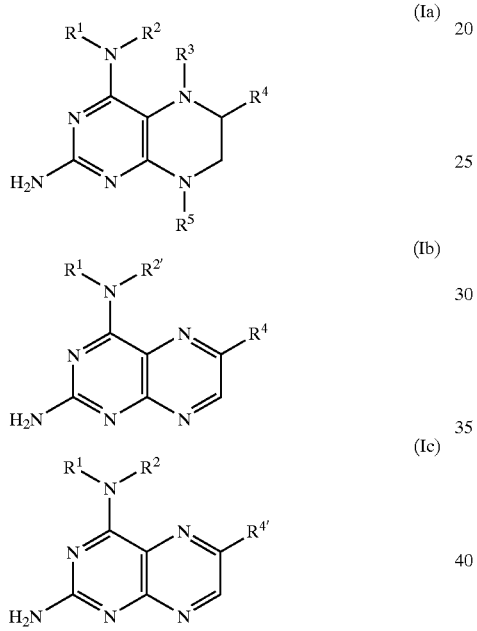

$R^1$ is hydrogen, $C_1$–$C_{20}$-alkyl, $C_2$–$C_{20}$-alkenyl, $C_2$–$C_{20}$-alkynyl, cycloalkyl with three to eight ring carbon atoms, cycloalkenyl with three to eight ring carbon atoms, cycloalkylalkyl with five to six ring carbon atoms, aryl, heteroaryl, alkylaryl, alkylheteroaryl, arylalkyl, heteroarylalkyl, wherein $R^1$ is unsubstituted or substituted with at least one substituent chosen from $R^6$, $R^2$ is $C_1$–$C_{20}$-alkyl, $C_2$–$C_{20}$-alkenyl, $C_2C_{20}$-alkynyl, cycloalkyl with three to eight ring carbon atoms, cycloalkenyl with three to eight ring carbon atoms, cycloalkylalkyl with five to six ring carbon atoms, aryl, heteroaryl, alkylaryl, alkylheteroaryl, arylalkyl, or heteroarylalkyl wherein $R^2$ is unsubstituted or substituted with at least one substituent chosen from $R^6$, $R^{2'}$ is $C_2$–$C_{20}$-alkenyl, $C_2$–$C_{20}$-alkynyl, cycloalkenyl with three to eight ring carbon atoms, cycloalkylalkyl with five to six ring carbon atoms, aryl, heteroaryl, alkylaryl, alkylheteroaryl, arylalkyl, or heteroarylalkyl wherein $R^{2'}$ is unsubstituted or substituted with at least one substituent chosen from $R^6$, or $R^1$ and $R^2$, together with the nitrogen atom bearing them, form a 3–8-membered ring which may optionally comprises 0, 1 or 2 further heteroatoms chosen from N, O, and S, and wherein said 3–8-membered ring is unsubstituted or substituted by at least one substituent chosen from $R^6$, $R^3$ is hydrogen, —CO-alkyl, —CO-alkylaryl, —CO-alkylheteroaryl, —CO-aryl, or —CO-heteroaryl, $R^4$ is $C_1$–$C_{20}$-alkyl, $C_2$–$C_{20}$-alkenyl, $C_2$–$C_{20}$-alkynyl, cycloalkyl with three to eight ring carbon atoms, cycloalkenyl with three to eight ring carbon atoms, cycloalkylalkyl with five to six ring carbon atoms, aryl, heteroaryl, alkylaryl, alkylheteroaryl, arylalkyl, heteroarylalkyl, —CO—O-alkyl, —CO—O-aryl, —CO—O-heteroaryl, —CO-alkyl, —CO-aryl or —CO-heteroaryl wherein $R^4$ is unsubstituted or substituted with at least one substituent chosen from $R^7$, $R^{4'}$ is $C_2$–$C_{20}$-alkenyl, $C_2$–$C_{20}$-alkynyl, cycloalkyl with three to eight ring carbon atoms, cycloalkenyl with three to eight ring carbon atoms, cycloalkylalkyl with five to six ring carbon atoms, heteroaryl, alkylheteroaryl, heteroarylalkyl, —CO—O-alkyl, —CO—O-aryl, —CO—O-heteroaryl, —CO—O-aryl or —CO—O-heteroaryl wherein $R^{4'}$ is unsubstituted or substituted with at least one substituent chosen from $R^7$, $R^5$ is hydrogen, —CO-alkyl, —CO-alkylaryl, —CO-alkylheteroaryl, —CO-aryl, or CO-heteroaryl, $R^6$ is —F, —OH, —O—($C_1$–$C_{10}$)alkyl, —O-phenyl, —O—CO—($C_1$–$C_{10}$)alkyl, —O—CO-aryl, —O—CO-heteroaryl, —NR$^8$R$^9$, oxo, phenyl, —CO—($C_1$–$C_5$)-alkyl, —CF$_3$, —CN, —CONR$^8$R$^9$, —COOH, —CO—O—($C_1$–$C_5$)-alkyl, —CO—O-aryl, —CO—O-heteroaryl, —S(O)$_n$—($C_1$–$C_5$)-alkyl, —SO$_2$NR$^8$R$^9$, $R^7$ is —F, —OH, —O—($C_1$–$C_{10}$)-alkyl, —O-phenyl, —O—CO—($C_1$–$C_{10}$)-alkyl, O—CO—O-aryl, O—CO—O-heteroaryl, —NR$^8$R$^9$, oxo, phenyl, —CO—($C_1$–$C_5$)-alkyl, —CF$_3$, —CN, —CONR$^8$R$^9$, —COOH, —CO—O—($C_1$–$C_5$)alkyl, —CO—O-aryl, —S(O)$_n$—($C_1$–$C_5$)alkyl, —SO$_2$—NR$^8$R$^9$, $R^8$ is hydrogen or $C_1$–$C_{20}$-alkyl, and $R^9$ is hydrogen, $C_1$–$C_{20}$-alkyl, aryl, or heteroaryl, wherein aryl groups are carbocyclic aryl groups, wherein heteroaryl groups are 5- to 7-membered unsaturated heterocycles comprising 1–4 heteroatoms chosen from O, N, and S, or a physiologically acceptable salt, hydrate, or ester thereof, in any stereoisomeric or tautomeric form.

2. The compound of the formula (Ia) as claimed in claim 1, in which $R^1$ is hydrogen, ($C_1$–$C_{10}$)-alkyl, ($C_3$–$C_8$)cycloalkyl, cycloalkylalkyl, aryl, heteroaryl, ($C_1$–$C_3$)alkylaryl, ($C_1$–$C_3$)alkylheteroaryl, arylalkyl, or heteroarylalkyl, wherein $R^1$ is unsubstituted or the alkyl radicals are substituted with at least one substituent chosen from $R^6$, $R^2$ is ($C_1$–$C_{10}$)alkyl, ($C_3$–$C_8$)cycloalkyl, cycloalkylalkyl, aryl, heteroaryl, ($C_1$–$C_3$)-alkylaryl, or ($C_1$–$C_3$) alkylheteroaryl wherein $R^2$ is unsubstituted or the alkyl radicals are substituted with at least one substituent chosen from $R^6$, or $R^1$ and $R^2$ may, together with the nitrogen atom bearing them, form a 3–8-membered ring, wherein said 3–8-membered ring optionally comprises 0, 1 or 2 further heteroatoms chosen from N, O, and S and wherein said 3–8-membered ring is unsubstituted or substituted by at least one substituent chosen from $R^6$, $R^3$ is hydrogen, —CO—$(C_1$–$C_7)$-alkyl, —CO—$(C_1$–$C_3)$ alkylaryl, —CO—$(C_1$–$C_3)$-alkylheteroaryl, —CO-aryl, or —CO-heteroaryl, $R^4$ is $(C_1$–$C_{10})$alkyl, aryl, heteroaryl, $(C_1$–$C_3)$-alkylaryl, $(C_1$–$C_3)$-alkylheteroaryl —CO—O—$(C_1$–$C_5)$-alkyl, —CO—O-aryl, —CO—O-heteroaryl, —CO—$(C_1$–$C_5)$alkyl, —CO-aryl or —CO-heteroaryl, wherein $R^4$ is unsubstituted or the alkyl radicals are substituted with at least one substituent chosen from $R^7$, $R^5$ is hydrogen, CO—$(C_1$–$C_7)$-alkyl, —CO—$(C_1$–$C_3)$-alkylaryl, —CO—$(C_1$–$C_3)$alkylheteroaryl, —CO-aryl, or —CO-heteroaryl, $R^6$ is —F, —OH, —O—$(C_1$–$C_{10})$-alkyl, —O-phenyl, —O—CO-$(C_1$–$C_{10})$alkyl, —O—CO-aryl, —O—CO-heteroaryl, —$NR^8R^9$, oxo, phenyl, —CO—$(C_1$–$C_5)$-alkyl, —$CF_3$, —CN, —$CONR^8R^9$, —COOH, —CO—O—$(C_1$–$C_5)$-alkyl, —CO—O-aryl, —CO—O-heteroaryl, —$S(O)_n$—$(C_1$–$C_5)$-alkyl, —$SO_2NR^8R^9$, $R^7$ is —F, —OH, —O—$(C_1$–$C_{10})$-alkyl, —O-phenyl, —O—CO—$(C_1$–$C_{10})$-alkyl, —O—CO-aryl, —O—CO-heteroaryl, —$NR^8R^9$, oxo, phenyl, —CO—$(C_1$–$C_5)$-alkyl, —$CF_3$, —CN, —$CONR^8R^9$, —COOH, —CO—O—$(C_1$–$C_5)$-alkyl, —CO—O-aryl, —CO—O-heteroaryl, —$S(O)_n$—$(C_1$–$C_5)$-alkyl, —$SO_2$—$NR^8R^9$, $R^8$ is hydrogen or $(C_1$–$C_5)$alkyl, and $R^9$ is hydrogen, $(C_1$–$C_5)$-alkyl or phenyl, wherein each aryl group is phenyl or naphthyl, and wherein said heteroaryl groups are 5- to 7-membered unsaturated heterocycles comprising 1–4 heteroatoms chosen from O, N, and S, wherein said phenyl, naphthyl and heteroaryl groups are substituted groups which are substituted by at least one substituent chosen from halogen, $(C_1$–$C_5)$-alkyl or phenyl, —OH, —O—$(C_1$–$C_5)$-alkyl, $(C_1$–$C_2)$-alkylenedioxy, —$N^8R^9$, —$NO_2$, —CO—$(C_1$–$C_5)$alkyl, —$CF_3$, —CN, —$CONR^8R^9$, —COOH, —CO—O—$(C_1$–$C_5)$alkyl, —S(O)—$_n$—$(C_1$–$C_5)$-alkyl, —$SO_2$—$NR^8R^9$, wherein n is 0, 1 or 2, or a physiologically acceptable salt, hydrate, or ester thereof, in any stereoisomeric or tautomeric form.

3. A compound of the formula (Ia) as claimed in claim 1, in which $R^1$ is hydrogen, unsubstituted $(C_2$–$C_4)$alkyl, substituted $(C_{2-C4})$alkyl which is substituted by at least one $R^6$, or $(C_1$–$C_2)$alkyl aryl or $(C_1$–$C_2)$-alkylheteroaryl, $R^2$ is unsubstituted $(C_{2-C4})$-alkyl, substituted $(C_{2-C4})$-alkyl which is substituted by at least one $R^6$, or cyclohexylmethyl or $(C_1$–$C_2)$-alkylaryl or $(C_1$–$C_2)$ alkylheteroaryl, or $R^1$ and $R^2$, together with the nitrogen atom bearing them, form a 5–7-membered ring wherein said 5–7-membered ring optionally comprises an additional heteroatom chosen from N, O, and S, $R^3$ is hydrogen, —CO—$(C_1$–$C_3)$-alkyl, —CO-aryl or —CO-heteroaryl, $R^4$ is aryl, heteroaryl, $(C_1$–$C_5)$alkyl, —CO—O-aryl or —CO-heteroaryl, wherein $R^4$ is unsubstituted or substituted with at least one substituent chosen from $R^7$, $R^5$ is hydrogen, $R^6$ is —OH, —O—$(C_1$–$C_3)$-alkyl, —$NR^8R^9$ or —COOH, and $R^7$ is —OH, $(C_1$–$C_{10})$-alkyloxy, phenoxy or oxo, wherein each aryl group is phenyl, wherein said heteroaryl groups are chosen from thiophenyl, furyl and pyridyl, wherein said phenyl, thiophenyl, furyl or pyridyl groups are unsubstituted groups or substituted groups which are substituted by at least one substituent chosen from $(C_{1-C3})$-alkyl, halogen, $(C_1$–$C_3)$alkyloxy and $(C_1$–$C_2)$-alkylenedioxy, and or a physiologically acceptable salt, hydrate, or ester thereof, in any stereoisomeric or tautomeric form.

4. A compound of the formula (Ia) as claimed in claim 1, in which $R^1$ is arylmethyl, $R^2$ is arylmethyl or cyclohexylmethyl, or $R^1$ and $R^2$, together with the nitrogen atom bearing them, form a pyrrolidine, piperidine, morpholine, dimethylmorpholine, thiomorpholine, or N-$(C_1$–$C_2)$ alkylpiperazine ring, $R^3$ is hydrogen, $R^4$ is aryl or 1,2-dihydroxypropyl, $R^5$ is hydrogen, $R^6$ is —OH, —O—$(C_1$–$C_3)$-alkyl, —$NR^8R^9$ or —COOH, and $R^7$ is —OH, decyloxy or phenoxy, wherein each aryl group is chosen from unsubstituted phenyl or substituted phenyl, which is substituted by at least one substituent chosen from $(C_1$–$C_3)$-alkyl, halogen and $(C_1$–$C_3)$ alkyloxy and $(C_1$–$C_2)$alkylenedioxy, or a physiologically acceptable salt, hydrate, or ester thereof, in any stereoisomeric or tautomeric form.

5. The compound of formula (Ia) as claimed in claim 1, which is a tetrahydropteridine wherein $R^4$ is aryl, heteroaryl, $(C_1$–$C_5)$-alkyl —CO—O-aryl or —CO—O-(heteroaryl), and wherein said $R^4$ is unsubstituted or substituted with at least one substituent chosen from $R^7$.

6. The compound of formula (Ia) as claimed in claim 1, wherein $R^1$ and $R^2$ are each, independently alkyl aryl, or heteroaryl, or $R^1$ is hydrogen and $R^2$ is cycloalkyl or cycloalkylalkyl, and wherein $R^4$ is aryl, $(C_1$–$C_5)$alkyl —CO—O-aryl or —CO—O-(heteroaryl), wherein said $R^4$ is unsubstituted or substituted with at least one substituent chosen from $R^7$.

7. A process for preparing a compound of formula (Ia), (Ib), or (Ic) as claimed in claim 1 comprising reacting a compound of the formula II

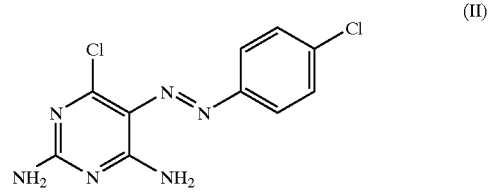

with a compound of the formula III $HNR^1R^2$ (III)

which results in a compound of the formula IV

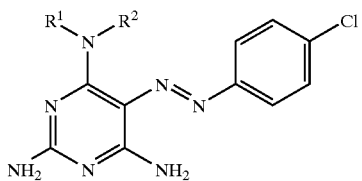
(IV)

wherein the compound of formula IV is converted to a compound of formula V by catalytic hydrogenation

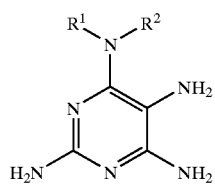
(V)

and wherein a compound of formula V is reacted with a compound of the formula VI

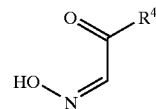
(VI)

to give a compound of formula (Ia), (Ib), or (Ic).

8. A pharmaceutical comprising a compound of formula (Ia), (Ib), or (Ic) as claimed in claim 1 and an additional ingredient chosen from conventional excipients and additives.

9. A method of treating or preventing strokes comprising administration of at least one pharmaceutical of claim 8 to a patient in need thereof.

* * * * *